United States Patent
Chen et al.

(10) Patent No.: US 8,063,017 B2
(45) Date of Patent: Nov. 22, 2011

(54) PROCESS FOR PREPARING PEPTIDE PRODUCTS FOR PROMOTING CHOLECYSTOKININ SECRETION AND USE OF THE PEPTIDE PRODUCTS

(75) Inventors: Yi-Hong Chen, Hsinchu (TW); Yu-Hui Liu, Hsinchu (TW); Chu-Chin Chen, Hsinchu (TW); Shiao-Cheng Chuang, Hsinchu (TW); Hsiang-Ling Lai, Hsinchu (TW); Chien-Ti Chang, Hsinchu (TW); Ming-Yu Hung, Hsinchu (TW); Su-Er Liou, Hsinchu (TW); Fu-Ning Chien, Hsinchu (TW)

(73) Assignee: Food Industry Research and Development Institute, Hsinchu (TW)

(*) Notice: Subject to any disclaimer, the term of this patent is extended or adjusted under 35 U.S.C. 154(b) by 229 days.

(21) Appl. No.: 12/332,677

(22) Filed: Dec. 11, 2008

(65) Prior Publication Data
US 2009/0239809 A1 Sep. 24, 2009

(30) Foreign Application Priority Data
Mar. 19, 2008 (TW) .............................. 97109668 A

(51) Int. Cl.
*A61K 38/00* (2006.01)
*A61P 3/04* (2006.01)

(52) U.S. Cl. ........................................ 514/4.9; 514/4.8

(58) Field of Classification Search .................. None
See application file for complete search history.

(56) References Cited

U.S. PATENT DOCUMENTS

| 3,170,802 | A | * | 2/1965 | Fukushima | 426/46 |
| 3,897,570 | A | * | 7/1975 | Yokotsuka et al. | 426/46 |
| 4,100,024 | A | * | 7/1978 | Adler-Nissen | 435/68.1 |
| 4,324,805 | A | * | 4/1982 | Olsen | 426/46 |
| 5,827,517 | A | | 10/1998 | Cook et al. | |
| 6,171,640 | B1 | * | 1/2001 | Bringe | 426/656 |
| 6,869,621 | B2 | | 3/2005 | Hwang et al. | |
| 6,884,454 | B2 | | 4/2005 | Pimentel | |

FOREIGN PATENT DOCUMENTS

| CN | 1544646 A | 11/2004 |
| EP | 0296574 A2 | 12/1988 |
| JP | 9-285266 A | 11/1997 |
| JP | 2002-20312 A | 1/2002 |
| JP | 2002-142723 A | 5/2002 |
| JP | 2004-010569 A | 1/2004 |
| JP | 2004-10569 A | 1/2004 |
| JP | 2004-159637 A | 6/2004 |

OTHER PUBLICATIONS

Office Action with Search Report Dated Feb. 18, 2011 Issued by the Intellectual Property Office of Taiwan in ROC (Taiwan) Patent Application No. 097109668 with English Translation of the Search Report Attached.

* cited by examiner

*Primary Examiner* — Marcela M Cordero Garcia
(74) *Attorney, Agent, or Firm* — Connolly Bove Lodge & Hutz, LLP

(57) ABSTRACT

A process for producing a peptide product having cholecystokinin secretion promoting effect, said process comprising hydrolyzing soybean residues with one or more proteases so that the peptide product having cholecystokinin secretion promoting effect is obtained. Also disclosed is the composition containing the peptide product and the use thereof.

14 Claims, 5 Drawing Sheets

PROCESS FOR PREPARING PEPTIDE PRODUCTS FOR PROMOTING CHOLECYSTOKININ SECRETION AND USE OF THE PEPTIDE PRODUCTS

FIELD OF THE INVENTION

The present invention elates to a novel process for producing peptide products. More particularly, the invention relates to a novel process comprising hydrolyzing soybean residues with one or more proteases so that the soybean peptide having cholecystokinin secretion promoting effect is obtained.

BACKGROUND OF THE INVENTION

Obesity has become a worldwide problem. Medical and nutrition experts have been paying much attention to the problem and trying to find solutions. Decreasing appetite and food intake and maintaining low food intake are considered effective ways to deal with the obesity problem. Accordingly, many nutraceuticals providing satiety are developed.

Satiety is controlled by many factors, among which neuropeptides are of significant importance. Cholecystokinin (CCK), a group of neuropeptides secreted by mucosal cells of intestine, has been shown to promote release and secretion of digestive enzymes from gallbladder and pancreas into intestine and produce satiety signals, which can inhibit desire for food intake.

CCK is produced by intestinal I cells within the intestinal mucosa (Buchan et al., Gut, 1978, 19:403-407). The intestinal I cells have a roughly triangular shape with their apical surface oriented toward the intestinal lumen of the intestine and secretary granules containing CCK concentrated around the base. The orientation allows the cells to be stimulated by nutrients and release CCK into the blood and/or surrounding tissue (Moran and Kinzig, Am. J. Physiol. Gastrointest. Liver Physiol., 2004, 286:G183-G188). CCK must binds to receptors located in gastric and duodenal vagus to induce a series of physiological activity (Moran et al., Am. J. Physiol. Regul, Integr. Comp. Physiol., 1997, 272:R1245-R1251). Furthermore, CCK receptors are also found in central nervous system. Therefore, CCK influences not only digestion but also secretion of other neurohormones, interacting with CCK to influence food intake (Woods, Am. J. Physiol. Gastrointest. Liver Physiol., 2004, 286:G7-G13). For example, Gutzwiller et al. reported the interaction between CCK-33 and glucagons-like peptide-1 (GLP-1) in inhibiting food intake and appetite in men (Gutzwiller et al., Am. J. Physiol. Regul. Integr. Comp. Physiol., 2004, 287:562-567). Moreover, CCK is a neuropeptide that produces satiety signals and is found to have interactions with adiposity signal leptin or insulin (Bado et al., Nature, 1998, 394:790-793; Brzozowski et al., Eur. J. Pharmacol., 1999, 374:363-376; Gallmann et al., Peptides, 2005, 26:437-445; Morton et al., J. Clin. Invest., 2005, 115: 703-710). In view of the above, CCK plays an important role in food intake of animals.

It was found that many nutrients in food had CCK secretion inducing effect, especially proteins and lipids. Low carbohydrate diet, or Atkins diet popular in Western countries, was developed on the basis of the theory However, research has revealed that proteins and lipids are more effective in promoting CCK secretion in animals if they are in the form of peptides and fatty acids. For example, Nishi et al. demonstrated in 2001 that peptic hydrolysates of proteins stimulated CCK release (Nishi et al., Exp. Biol. Med., 2001, 226:1031-1036). In that study, they examined the direct effects of peptic hydrolysates of naturally occurring dietary proteins and found that hydrolysate of soybean protein isolate was the most effective in stimulating CCK release. Moreover, they found that the most bioactive peptide was the soybean β-conglycinin β51-63 fragment (Nishi et al., J. Nutr., 2003, 133: 352-357). The amino acid composition and hydrophobicity of peptides may have to do with their CCK secretion inducing effect (Furuse et al., Comp. Biochem. Physiol., 1991, 99A: 449-451; Backus et al., Regul. Pept., 1997, 72:31-40). Bernard et al. demonstrated that peptones stimulated intestinal cholecystokinin gene transcription via cyclic adenosine monophosphate response element-binding factors (Bernard et al., Endocrinology, 2001, 142:721-729).

JP2004010569 discloses an arginine-containing peptide having a CCK secretion promoting activity. The peptide is obtained by the decomposition of purified soybean β-conglycinin with a pepsin and is soybean β-conglycinin β 51-63 fragment. However, the starting materials used in JP2004010569 must be pretreated through complex purification steps and, accordingly, is more cost-ineffective. Therefore, there still exists a need for a more efficient and cost-effective method of producing peptides having a CCK secretion promoting effect.

Surprisingly the inventors discovered that one could treat soybean residues, which need not be pre-purified, with proteases to obtain peptides having a CCK secretion promoting activity. The peptide can increase satiety of animals so as to decrease their food intake and achieve the effect of weight control.

SUMMARY OF THE INVENTION

The present invention relates to a process for producing a peptide product by using soybean residues as starting materials. The peptide product has the effect of promoting CCK secretion, increasing satiety and lowering food intake, and, accordingly, is effective in weight control.

In another embodiment, the present invention relates to a soybean peptide product having a CCK secretion promoting effect.

In a further embodiment, the present invention provides a composition containing a soybean peptide product having a CCK secretion promoting effect.

DETAILED DESCRIPTION OF THE INVENTION

Figure 1:
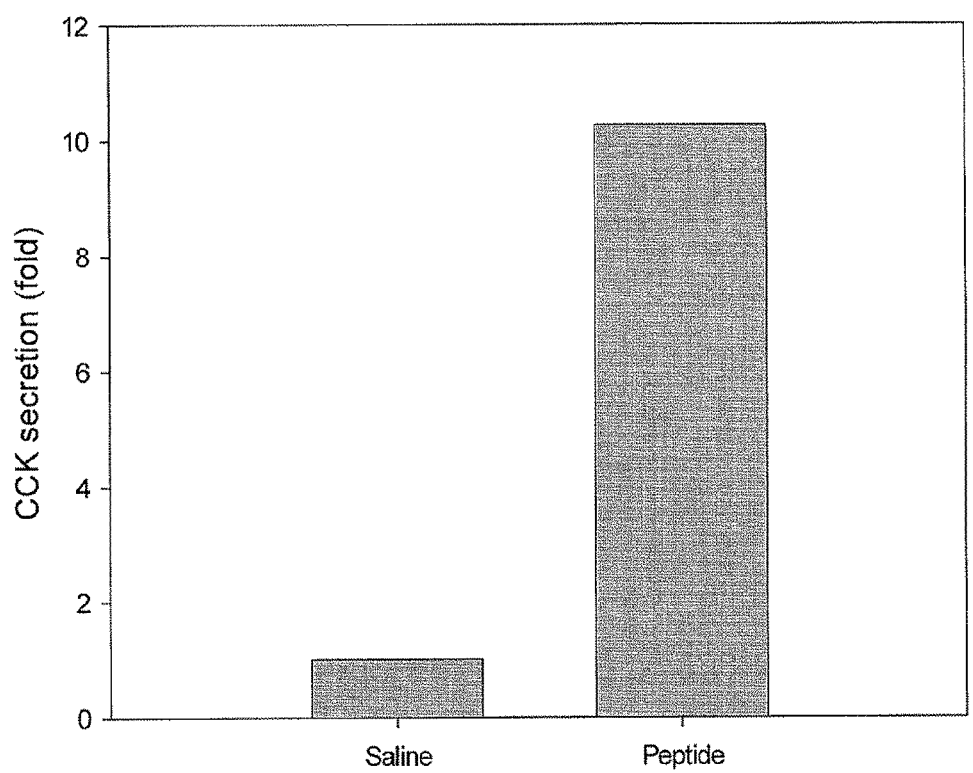
FIG. 1 shows the CCK secretion promoting effects of the peptide product on intestinal mucosal cells.

The invention provides a process for the preparation of a peptide product for promoting secretion of cholecystokinin (COCK), comprising the following steps:
(a) mixing a soybean residue with water;
(b) hydrolyzing the mixture obtained in step (a) with a protease at a suitable temperature;
(c) making the protease in the hydrolysate obtained in step (b) inactive;
(d) separating the liquid from the solid of the mixture of step (c) and collecting the liquid so as to obtain the peptide product.

As used herein, the term "soybean residue" refers to a solid waste of defatted soybean powder, which is obtained by defatting soybeans left after a process of producing nutritional soybean peptides. The process of producing nutritional soybean peptides comprises mixing defatted soybean powder with water, adding *Aspergillus sojae* to the mixture to make it ferment and hydrolyze, and removing the liquid from the fermented and hydrolyzed mixture. The resulting solid waste is the soybean residue. Generally, soybean residue contains about 30% (w/w) of solids and about 15% (w/w) of crude proteins.

According to the invention, soybean residue is mixed with water which is in an amount of a bout 0.5 to about 10 times (w/w) the weight of the soybean residue. Preferably, the soybean residue is mixed with water which is in an amount of about 1 to about 5 times (w/w) thew eight of the soybean residue. More preferably, the soybean residue is mixed with water which is in an amount of about 3 times (w/w) the weight of the soybean residue.

As used herein, "protease" refers to any commercially available products or enzymes derived from microorganisms, animals or plants and has a protein hydrolyzing activity. The protease of the invention can be endoproteases, exopeptidases or the combinations thereof. The protease of the invention includes, but is not limited to, thermolysin, pepsin, trypsin, bromelain, Alcalase (Novozyme), Flavorzyme, Esperase, PTN 6.0 S, Acid Protease, Protease A, Protease M, Protease N, Protease NL, Protease P, Protease S, Protin S. Dak., Thermoase, Flavorpro and Promod. Preferably, the protease is Alcalase.

According to the invention, the amount of protease added in the hydrolysis reaction depends on the species of protease used. The protease is added in a n amount of about 10,000 I.U. to about 125,000 I.U. per kilogram of soybean residues. Preferably, the protease is added in an amount of a bout 10,000 I.U. to about 80,000 I.U. More preferably, the protease is added in an amount of about 10,000 I.U. to about 40,000 I.U.

In the embodiment where the protease used is Alcalase, it is added in an amount of about 20,000 I.U. to about 125,000 I.U. Preferably, the protease is added in an amount of about 20,000 I.U. to about 80,000 I.U. More preferably, the protease is added in an amount of about 20,000 I.U. to about 30,000 I.U.

According to the invention, the time and temperature of the hydrolysis reaction depend on the species of protease used. The time of the hydrolysis reaction ranges from about 1 to about 24 hours, preferably from about 1 to about 8 hours, and more preferably from about 2 to about 4 hours. The temperature of the hydrolysis reaction ranges from about 30° C. to about 60° C., preferably from about 40° C. to about 55° C., and more preferably from about 45° C. to about 55° C.

In the embodiment where the protease used is Alcalase, the time of the hydrolysis reaction ranges from about 1 to about 16 hours, preferably from about 2 to about 8 hours, and more preferably is about 2 hours. The temperature of the hydrolysis reaction ranges from about 30° C. to about 55° C., preferably from about 50° C. to about 55° C., and more preferably is about 50° C.

According to the method of the invention, the step of inactivating the proteases in the hydrolysate can be carried out by any methods known to persons having ordinary skill in the art. For example, methods suitable for use in the invention include, but are not limited to, heating, pH adjustment, pressurization, and any combinations thereof. In one embodiment of the invention, the step of inactivating the protease comprises heating the hydrolysate to about 80 to about 100° C., preferably to about 85 to 95° C., and more preferably to about 90° C.

According to the method of the invention, the step of separating the liquid from the solid of the hydrolysate and collecting the liquid so as to obtain the peptide product of the invention can be carried out by any methods known to persons having ordinary skill in the art. For example, methods suitable for use in the invention include, but are not limited to, filtration, centrifugation, press-filtration, sedimentation, or any combinations thereof. In one embodiment of the invention, the step of separating the liquid from the solid of the hydrolysate is carried out by press-filtration, wherein the hydrolysate is treated with a filter press.

According to the method of the invention, the liquid collected from the hydrolysate is further concentrated and dried so that a concentrated and dried peptide product is obtained. The concentrating and drying methods are known to persons having ordinary skill in the art and include, but are not limited to, lyophilization, spray drying, drum-dryer drying, fluid-bed drying, and a ny combinations thereof. Preferably, the concentrating and drying method of the invention is spray drying.

In a further embodiment of the invention, a soybean peptide product produced by the above method is provided. The peptide product is useful in promoting CCK secretion and increasing animal satiety and, accordingly, can help lower food intake and control weight.

In a further embodiment of the invention, a composition containing the soybean peptide product is provided. The composition of the invention is a pharmaceutical composition or a food composition. The pharmaceutical composition or food composition can be prepared in a conventional manner by mixing the peptide product with one or more conventional carriers, diluents, solvents, colorants, anti-oxidants, inert materials and/or other additives to formulate the composition in the form of tablets, capsules, powder, pellets, concentrates, beverages, nutraceuticals, food additives or feeds.

In a further embodiment of the invention, a method for promoting secretion of CCK in a subject in need thereof is provided, which comprises administering an effective amount of the peptide product of claim 14 to the subject. According to the invention, the subject is a human or an animal. Preferably, the subject is a human. Due to the promoted secretion of CCK, the appetite of the subject can be inhibited.

EXAMPLES

Example 1

Preparation of Soybean Residues

The soybean residues were wastes of the process of producing nutritional soybean peptides. First, 25 kg of defatted soybean powder (purchased from Central Union Oil Corp.) were mixed with water which was half the weight of the defatted soybean powder; the mixture was steamed with steam of 100° C. for 45 minutes and then cooled to 45° C. 4.2 g of koji (purchased from Higuchi Matsunosuke Shouten Co Ltd. Japan) containing *Aspergillus sojae* were added to the mixture and mixed, and the mixture was fermented under 27° C. and 95% relative humidity for 48 hours. After fermentation, water 3 times the weight of the fermented mixture was added to the mixture and the mixture was hydrolyzed at 45° C. for 8 hours. Then the hydrolysates containing mixture of solid and liquid were put into a filter press (purchased from Klinkau GmbH & Co.) by using a pump. Each chamber of the filter plates and frames contained a filter cloth with a pore size of 1,000 mesh. After the hydrolysates were put into the filter press, the pressure in the chamber was increased to 200-250 k g/cm² so as to separate the fluid from the solid filter cake. The liquid was nutritional soybean peptides, and the solid filter cake remaining on the filter cloth was the soybean residue. The soybean residue obtained from the above method contained 30% (w/w) solids and 15% (w/w) crude proteins.

Example 2

Preparation of Powdered Satiety Peptides with Alcalase

Soybean residue prepared by the process of Example 1 was mixed with water which was 3 times the weight of the soybean residue. The pH of the mixture was adjusted to 9.0 and 24 A.U. (about 27,360 I.U.) of Alcalase (purchased from Novazyme) were added for every kilogram of soybean residue. The mixture was hydrolyzed at 50° C. for 2 hours. The hydrolysate was heated to 90° C. for 10 minutes to inactive the enzyme. The liquid was separated from the solid of the hydrolysates using the filter press described in Example 1. The liquid was then collected and concentrated to the concentration of 40 brix by using evaporator MT-3 purchased from Mao Tai Machinery Co., Ltd. Taiwan. Finally, the concentrated liquid was spray dried to yield the powdered satiety peptides (the spray drier DA 360-100H was purchased from TS Technology Corp., Taiwan).

Example 3

Analysis of the Peptide Composition of the Satiety Peptides

The powdered peptides obtained from Example 2 were dissolved in water to prepare a 0.5% (w/w) water solution. The solution was divided into 20 fractions using a device for isoelectric focusing (Rotofor; Bio-Rad Laboratories, CA, USA) according to the instructions provided by the manufacturer. Each fraction was lyophilized and reconstituted to a suitable concentration. The reconstituted solution was used in the analysis of peptide composition by high performance liquid chromatography (HPLC). 43 peptides in total were identified (Table 1).

The equipment and conditions used in HPLC analysis are as follows: High Performance Liquid Chromatography: Waters 600 pump (Milford, Mass., USA); Column: LiChroCART 125-2 Supersher 100 RP-18 column (Merck, Darmstadt, Germany);

Mass spectrometer: Micromass Quattro LC mass spectrometer (Wythenshawe, UK);

Elution solution: solution A is water and solution B is acetonitril; and

Elution condition: 15% solution B for 3 minutes, 15% solution B progressing linearly to 85% for 60 minutes, and 85% B solution for 7 minutes.

TABLE 1

Peptide composition of the satiety peptides

| Mass to charge ratio (m/z) | Retention time (min) | Sequence | SEQ ID NO: |
|---|---|---|---|
| 203 | 6.61 | Leu-Ala | 1 |
| 204 | 5.27 | Ala-Asn | 2 |
| 205 | 12.09 | Ser-Val | 3 |
| 231 | 8.15 | Val-Leu | 4 |
| 232 | 7.27 | Val-Asn | 5 |
| 232 | 8.82 | Val-Gly-Gly | 6 |
| 233 | 5.42 | Ser-Leu | 7 |
| 233 | 6.26 | Thr-Leu | 8 |
| 234 | 5.29 | Thr-Asn | 9 |
| 237 | 7.16 | Ala-Phe | 10 |
| 245 | 15.00 | Leu-Leu | 11 |
| 246 | 5.97 | Asn-Leu | 12 |
| 246 | 6.37 | Val-Gly-Ala | 13 |
| 260 | 3.89 | Leu-Gln | 14 |
| 260 | 6.39 | Gln-Leu | 15 |
| 263 | 4.59 | Met-Leu | 16 |
| 264 | 4.32 | Ser-Gly-Ser | 17 |
| 265 | 9.12 | Phe-Val | 18 |
| 265 | 12.49 | Val-Phe | 19 |
| 267 | 7.74 | Ser-Phe | 20 |
| 276 | 6.11 | Ser-Gly-Leu | 21 |
| 279 | 24.23 | Phe-Leu | 22 |
| 281 | 5.49 | Val-Tyr | 23 |
| 288 | 16.91 | Val-Gly-Leu | 24 |
| 295 | 6.92 | Phe-Glu | 25 |
| 295 | 9.12 | Leu-Tyr | 26 |
| 295 | 12.36 | Tyr-Leu | 27 |
| 296 | 12.18 | Tyr-Asn | 28 |
| 304 | 7.56 | Ala-Ser-Leu | 29 |
| 304 | 8.70 | Ala-Thr-Leu | 30 |
| 318 | 6.83 | Leu-Gly-Glu | 31 |
| 329 | 14.75 | Phe-Tyr | 32 |
| 329 | 19.15 | Tyr-Phe | 33 |
| 330 | 18.96 | Val-Val-Leu | 34 |
| 332 | 21.93 | Ser-Ile-Leu | 35 |
| 332 | 25.12 | Leu-Ser-Leu | 36 |
| 345 | 15.96 | Val-Gly-Gly-Leu | 37 |
| 348 | 6.57 | Leu-Ser-Glu | 38 |
| 352 | 16.93 | Val-Ala-Tyr | 39 |
| 352 | 23.09 | Val-Ser-Phe | 40 |
| 366 | 10.48 | Tyr-Ile-Ala | 41 |
| 374 | 3.91 | Lys-Val-Gln | 42 |
| 380 | 11.25 | Phe-Val-Asp | 43 |

Example 4

Effects of Satiety Peptides on Promoting CCK Secretion of Intestinal Mucosal Cells The intestinal mucosal cells were isolated from Spraque-Dawley (SD) rats according to the method described in Nishi et al, 2003. Briefly, the animals were fasted for 12 hours and sacrificed on the subsequent day. About 20 cm of intestine adjacent to the pylorus were isolated and immediately immersed in normal saline. After flushing with normal saline, the intestine was slit and immersed in calcium-free Krebs-Henseleit bicarbonate buffer (containing 2.5 mmol/L EDTA, pH 7.4) at 37° C. for 5 minutes. The intestinal inner surface was scraped with a Teflon scraper to obtain a suspension containing intestinal tissues and intestinal cells. The suspended intestinal tissues were removed from the suspension by filtration. After the suspended intestinal tissues were removed, the suspension was subjected to centrifugation to obtain the intestinal mucosal cells in a pellet. The pellet containing intestinal mucosal cells was resuspended in appropriate HEPES buffers. The Enzyme-Linked Immunosorbent Assay kit (Phoenix Pharmaceuticals, Inc. Belmont, Calif., USA) was used to detect CCK secretion of intestinal mucosal cells.

The results revealed that the CCK promoting effect of the satiety peptides on intestinal mucosal cells was about 10 times greater than was the normal saline group (FIG. 1).

Example 5

Inhibitory Effects of the Satiety Peptides on Animal Appetite

Male SD rats were placed in individual cages, acclimated to a 12-hour light/dark cycle at a room temperature kept at 23±2° C. A case in-based basal stock diet Test Diet 5800 (PMI Nutrition International, Richmond, Ind., USA) was provided and the animals were allowed to ingestit unrestrictedly. The animals were fasted for 4 hours before feeding test. Then, they were divided into experimental and control groups. In the experimental group, the peptide products obtained in Example 2 were dissolved in water at a concentration of 10 g/L and were administered in an amount of 1% (v/w) body weight of the animal by tube stomach feeding. In the control group, water of 1% (v/w) of the body weight of the animal was administered to the animal. After 10 minutes of administrations of satiety peptides or water, the animals were given 30 g of their basal stock diet and were allowed to ingest it unrestrictedly. The food consumption was determined 1, 2, and 3 hours after the basal stock diet was given.

Figure 2:
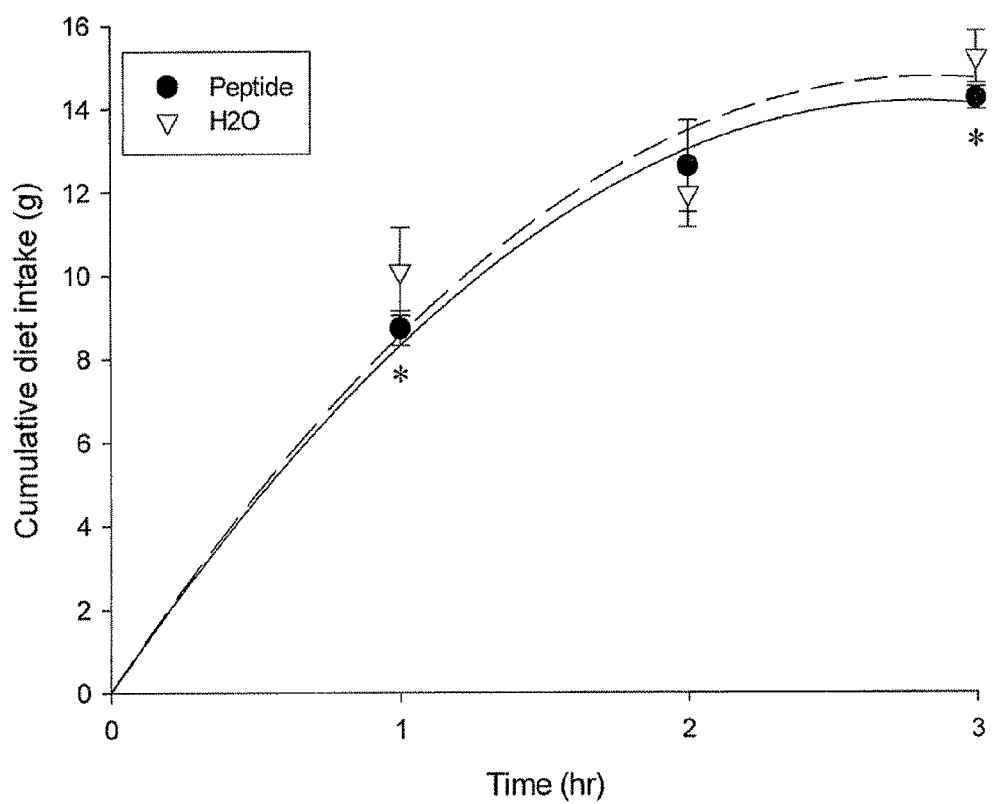
FIG. 2 shows the influence of the peptide product on food intake of SD rats within three hours of administration of the peptide product. Each value in the figure is a mean of food intake of eight rats ±95% confidence interval. * Significant difference between the experimental group and the control group (P<0.05).

The result revealed that food consumption of the experimental group was significantly lower than that of the control group within 1 hour of administration of the peptide product of the invention. It was concluded that the peptide product of the invention had an effect of inducing satiety in the animals and accordingly reduced their food consumption. Moreover, it was found that the satiety inducing effect was sustained for 3 hours after the peptide product was administered (FIG. 2).

Example 6

Effects of the Satiety Peptides on Animal's Body Weight

Male SD rats aged 4 weeks were placed in individuals ages, acclimated to a 12-hour light/dark cycle at a room temperature kept at 23±2° C. A casein-based basal stock diet TestDiet 5800(PMI Nutrition International, Richmond, Ind., USA) was provided and the animals were allowed to ingest it unrestrictedly. Diet training was performed one week before the test by gradually reducing the time during which the animals had access to the diet. Eventually, the animals were trained to be used to a feeding time of 3 hours per day.

The animals were divided into experimental and control groups. In the experimental group, the peptide products obtained in Example 2 were dissolved in water at a concentration of 20 g/L and were administered in an amount of 0.5% (v/w) body weight of the animal by tube stomach feeding 15 minutes prior to the dark period every day. In the control group, water of 0.5% (v/w) of the body weight of the animal was administered to the animals 15 minutes prior to the dark period every day. When the dark period started, sufficient basal stock diet was provided for 3 hours so that the animals could ingest it unrestrictedly. Food consumption within the 3 hour period was measured. The test was repeated every day for 13 weeks. The body weight change of the animals was measured every week.

Figure 3:
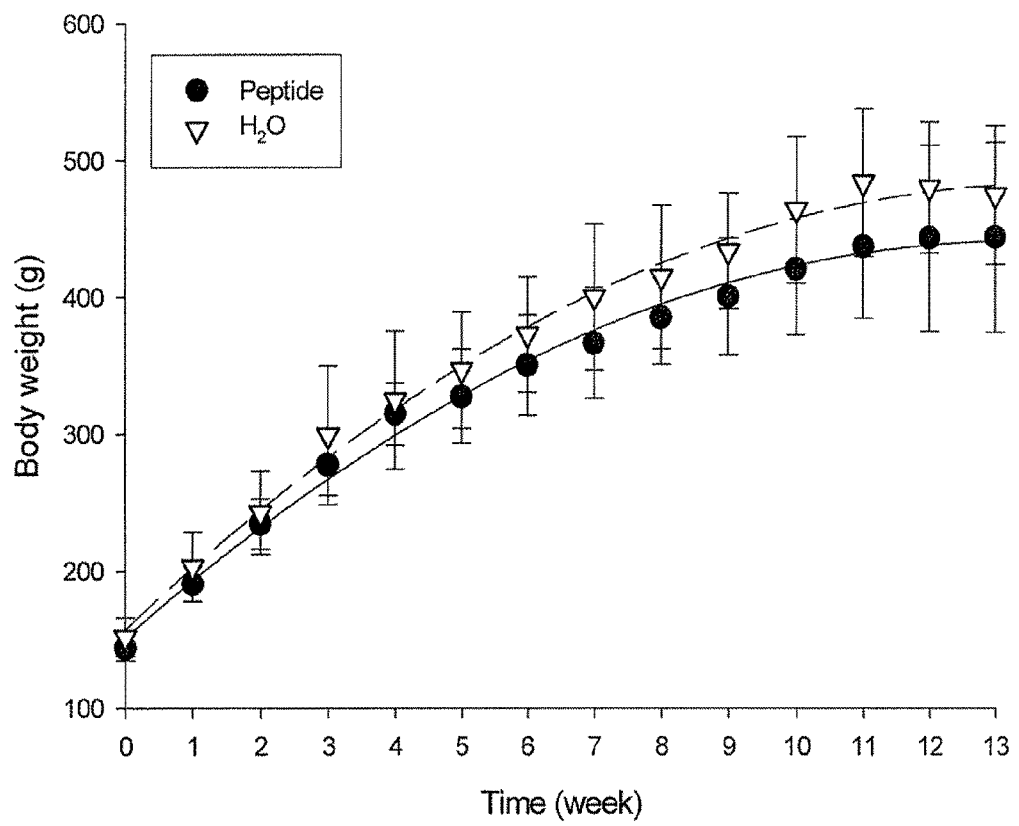
FIG. 3 shows the influence of the peptide product on body weight of SD rats. Each value in the figure is a mean of body weight of six rats ±95% confidence interval.

After a 13-week test, it was found that the mean body weight of the experimental group was lower than that of the control group (FIG. 3). It was presumed that the food consumption of the experimental group was reduced due to the administration of the peptide product of the invention for 13 weeks.

Example 7

Effects of the Satiety Peptides on Human Appetite 18 to 24 volunteers participated in the trial. The trial was performed on the basis of a two-day cycle, 5 cycles in total. On one day the volunteers were given 80 ml of commercially available instant soup dissolved in hot water at a concentration of 1.6% (w/v) 30 minutes before lunch, and on the other day, they were given 80 ml of the same soup further containing the peptide product of the invention 30 minutes before lunch. All the volunteers were then given the same lunch box on the two days. After lunch, the volunteers were required to fill in a questionnaire on their feeling of fullness and hunger 15 minutes before, 15 minutes after, and 30 minutes after drinking the soup and 30 minutes after eating lunch boxes. The feeling of fullness and hunger was evaluated on a scale from 1 to 7. Furthermore, the food consumption was also recorded.

Figure 4A:
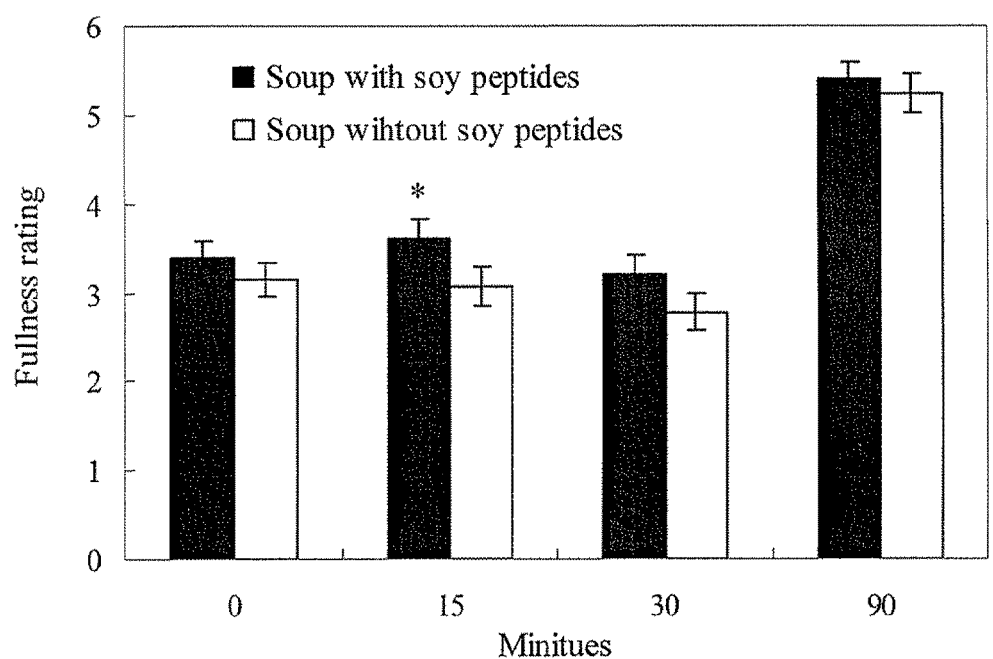
FIGS. 4(a) and 4(b) show the influence of the peptide product, added to soup, on satiety and appetite. Each bar is a mean of 5 cycles of trials ±95% confidence interval. The mean is derived from 104 questionnaires.
Figure 4B:
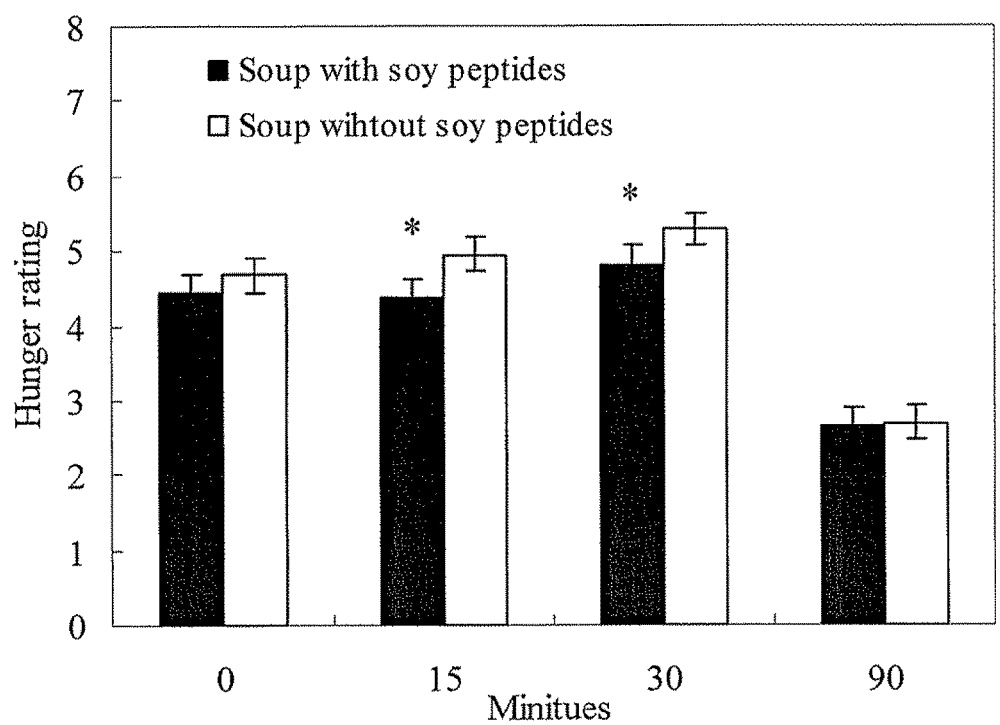

The results revealed that the volunteers felt a higher degree of fullness after drinking the soup containing the peptide product at each time point (FIG. 4(a)). The difference in feeling of fullness between the two days was the most significant 15 to 30 minutes after drinking the soup, especially 15 minutes after drinking the soup. Furthermore, all the volunteers felt a lower degree of hunger after drinking the soup containing the peptide product at each time point. The difference in feeling of hunger between the two days was the most significant 15 and 30 minutes after drinking the soup (FIG. 4(b)). The results indicated that the soup containing the peptide product of the invention was more effective in reducing hunger and increasing fullness than the soup without the peptide product. The effect was the most significant 15 to 30 minutes after drinking the soup, presumably because the effectiveness of the peptide product was related to the time in which it was sustained. Therefore, when the volunteers were given a meal 30 minutes after drinking the soup containing the peptide product, their food consumption decreased. Table 2 shows that in the 5-cycle trial, the food consumption of about 60% to 80% of the volunteers decreased.

TABLE 2

| | Effect of the peptide product on food consumption | | | | |
| --- | --- | --- | --- | --- | --- |
| | Cycle | | | | |
| | 1 | 2 | 3 | 4 | 5 |
| Difference in food consumption (g)[1)] | −81.6 | −105.5 | −117.5 | −91 | −70 |
| | −80.1 | −84.3 | −93.6 | −141 | −52 |
| | −55.3 | −69.3 | −57 | −112.7 | −51 |
| | −45.8 | −45.6 | −38.7 | −76 | −48.9 |

TABLE 2-continued

Effect of the peptide product on food consumption

| | Cycle | | | | |
|---|---|---|---|---|---|
| | 1 | 2 | 3 | 4 | 5 |
| | −35.7 | −45.4 | −17 | −67.2 | −48.8 |
| | −34.7 | −31.1 | −16 | −54 | −47 |
| | −33.9 | −24.3 | −7.4 | −48.6 | −38.7 |
| | −31.8 | −23.3 | −3.5 | −46 | −37.5 |
| | −30 | −15 | −3.4 | −42 | −35.4 |
| | −24.8 | −13.6 | −0.7 | −29.5 | −26.1 |
| | −16 | −7.5 | −0.2 | −28 | −25 |
| | −8 | −6.8 | 3 | −21.2 | −10.8 |
| | −3.6 | −6.8 | 4.4 | −13.5 | −3.8 |
| | −3.3 | −2 | 5.4 | −12.7 | −2.1 |
| | 7.9 | 1.6 | 11.1 | −7 | 15 |
| | 16.4 | 2.1 | 12.7 | −2.6 | 19.5 |
| | 26.1 | 23 | 38.7 | −2 | 45.9 |
| | 28 | 25.3 | 43 | 0.9 | 47 |
| | 37.8 | 27 | | 7.4 | 84.5 |
| | 46 | 34.5 | | 26 | |
| | 54.1 | 46.4 | | 29 | |
| | 91.8 | 70 | | | |
| | | 105.5 | | | |
| | | 107.9 | | | |
| Mean ± S.D.(g) | −8.0 ± 43.7 | −1.5 ± 52.2 | −13.2 ± 41.0 | −34.8 ± 44.1 | −15.0 ± 41.2 |
| Number of volunteers whose food consumption decreased, increased (−, +) | 14−, 8+ | 14−, 10+ | 11−, 7+ | 17−, 4+ | 14−, 5+ |
| Number of volunteers whose food consumption decreased/total number of the volunteers (%) | 63.60% | 58.30% | 61.10% | 80.90% | 73.70% |

[1])Difference in food consumption equals the food consumption on the day of drinking soup containing the peptide product minus the food consumption on the day of drinking soup without the peptide product.

The invention claimed is:

1. A process for the preparation of a peptide product for promoting secretion of cholecystokinin (CCK), comprising the following steps:
   (a) mixing a soybean residue with water;
   (b) hydrolyzing the mixture obtained in step (a) with a protease at a suitable temperature;
   (c) making the protease in the hydrolysate obtained in step (b) inactive;
   (d) separating the liquid from the solid of the mixture of step (c) and collecting the liquid so as to obtain the peptide product, wherein the soybean residue is obtained by mixing defatted soybean powder with water, adding *Aspergillus sojae* to the mixture to make it ferment and hydrolyze, and removing the liquid from the fermented and hydrolyzed mixture, and wherein the peptide product comprises the peptides of SEQ ID NO:s: 1-43.

2. The process according to claim 1, wherein the water is about 0.5 to about 10 times the weight of the soybean residues.

3. The process according to claim 2, wherein the water is about 1 to about 5 times the weight of the soybean residues.

4. The process according to claim 3, wherein the water is about 3 times the weight of the soybean residues.

5. The process according to claim 1, wherein the protease is an endoprotease, an exopeptidase or the combination thereof.

6. The process according to claim 5, wherein the protease is Alcalase.

7. The process according to claim 5, wherein the protease is in an amount of about 10,000 I.U. to about 125,000 I.U. per kilogram of the soybean residues.

8. The process according to claim 6, wherein the protease is in an amount of about 20,000 I.U. to about 125,000 I.U. per kilogram of the soybean residues.

9. The process according to claim 1, wherein the mixture is treated with the protease at about 30 to about 60° C. for about 1 to about 24 hours.

10. The process according to claim 6, wherein the mixture is treated with the protease at about 30 to about 55° C. for about 1 to about 16 hours.

11. The process according to claim 1, further comprising step (e) where the liquid collected from step (d) is concentrated and/or dried so that a concentrated and/or dried peptide product is obtained.

12. The process according to claim 11, wherein the liquid is dried by spray drying.

13. A method for promoting secretion of CCK in a subject in need thereof comprising administering an effective amount of the peptide product obtained by the process of claim 1 to the subject.

14. The method according to claim 13, wherein the secretion of CCK inhibits the appetite of the subject.

* * * * *

```
                          SEQUENCE LISTING

<160> NUMBER OF SEQ ID NOS: 43

<210> SEQ ID NO 1
<211> LENGTH: 2
<212> TYPE: PRT
<213> ORGANISM: Glycine max

<400> SEQUENCE: 1

Leu Ala
1

<210> SEQ ID NO 2
<211> LENGTH: 2
<212> TYPE: PRT
<213> ORGANISM: Glycine max

<400> SEQUENCE: 2

Ala Asn
1

<210> SEQ ID NO 3
<211> LENGTH: 2
<212> TYPE: PRT
<213> ORGANISM: Glycine max

<400> SEQUENCE: 3
```

Ser Val
1

<210> SEQ ID NO 4
<211> LENGTH: 2
<212> TYPE: PRT
<213> ORGANISM: Glycine max

<400> SEQUENCE: 4

Val Leu
1

<210> SEQ ID NO 5
<211> LENGTH: 2
<212> TYPE: PRT
<213> ORGANISM: Glycine max

<400> SEQUENCE: 5

Val Asn
1

<210> SEQ ID NO 6
<211> LENGTH: 3
<212> TYPE: PRT
<213> ORGANISM: Glycine max

<400> SEQUENCE: 6

Val Gly Gly
1

<210> SEQ ID NO 7
<211> LENGTH: 2
<212> TYPE: PRT
<213> ORGANISM: Glycine max

<400> SEQUENCE: 7

Ser Leu
1

<210> SEQ ID NO 8
<211> LENGTH: 2
<212> TYPE: PRT
<213> ORGANISM: Glycine max

<400> SEQUENCE: 8

Thr Leu
1

<210> SEQ ID NO 9
<211> LENGTH: 2
<212> TYPE: PRT
<213> ORGANISM: Glycine max

<400> SEQUENCE: 9

Thr Asn
1

<210> SEQ ID NO 10
<211> LENGTH: 2
<212> TYPE: PRT
<213> ORGANISM: Glycine max

<400> SEQUENCE: 10

Ala Phe
1

```
<210> SEQ ID NO 11
<211> LENGTH: 2
<212> TYPE: PRT
<213> ORGANISM: Glycine max

<400> SEQUENCE: 11

Leu Leu
1

<210> SEQ ID NO 12
<211> LENGTH: 2
<212> TYPE: PRT
<213> ORGANISM: Glycine max

<400> SEQUENCE: 12

Asn Leu
1

<210> SEQ ID NO 13
<211> LENGTH: 3
<212> TYPE: PRT
<213> ORGANISM: Glycine max

<400> SEQUENCE: 13

Val Gly Ala
1

<210> SEQ ID NO 14
<211> LENGTH: 2
<212> TYPE: PRT
<213> ORGANISM: Glycine max

<400> SEQUENCE: 14

Leu Gln
1

<210> SEQ ID NO 15
<211> LENGTH: 2
<212> TYPE: PRT
<213> ORGANISM: Glycine max

<400> SEQUENCE: 15

Gln Leu
1

<210> SEQ ID NO 16
<211> LENGTH: 2
<212> TYPE: PRT
<213> ORGANISM: Glycine max

<400> SEQUENCE: 16

Met Leu
1

<210> SEQ ID NO 17
<211> LENGTH: 3
<212> TYPE: PRT
<213> ORGANISM: Glycine max

<400> SEQUENCE: 17

Ser Gly Ser
1

<210> SEQ ID NO 18
<211> LENGTH: 2
```

```
<212> TYPE: PRT
<213> ORGANISM: Glycine max

<400> SEQUENCE: 18

Phe Val
1

<210> SEQ ID NO 19
<211> LENGTH: 2
<212> TYPE: PRT
<213> ORGANISM: Glycine max

<400> SEQUENCE: 19

Val Phe
1

<210> SEQ ID NO 20
<211> LENGTH: 2
<212> TYPE: PRT
<213> ORGANISM: Glycine max

<400> SEQUENCE: 20

Ser Phe
1

<210> SEQ ID NO 21
<211> LENGTH: 3
<212> TYPE: PRT
<213> ORGANISM: Glycine max

<400> SEQUENCE: 21

Ser Gly Leu
1

<210> SEQ ID NO 22
<211> LENGTH: 2
<212> TYPE: PRT
<213> ORGANISM: Glycine max

<400> SEQUENCE: 22

Phe Leu
1

<210> SEQ ID NO 23
<211> LENGTH: 2
<212> TYPE: PRT
<213> ORGANISM: Glycine max

<400> SEQUENCE: 23

Val Tyr
1

<210> SEQ ID NO 24
<211> LENGTH: 3
<212> TYPE: PRT
<213> ORGANISM: Glycine max

<400> SEQUENCE: 24

Val Gly Leu
1

<210> SEQ ID NO 25
<211> LENGTH: 2
<212> TYPE: PRT
<213> ORGANISM: Glycine max
```

```
<400> SEQUENCE: 25

Phe Glu
1

<210> SEQ ID NO 26
<211> LENGTH: 2
<212> TYPE: PRT
<213> ORGANISM: Glycine max

<400> SEQUENCE: 26

Leu Tyr
1

<210> SEQ ID NO 27
<211> LENGTH: 2
<212> TYPE: PRT
<213> ORGANISM: Glycine max

<400> SEQUENCE: 27

Tyr Leu
1

<210> SEQ ID NO 28
<211> LENGTH: 2
<212> TYPE: PRT
<213> ORGANISM: Glycine max

<400> SEQUENCE: 28

Tyr Asn
1

<210> SEQ ID NO 29
<211> LENGTH: 3
<212> TYPE: PRT
<213> ORGANISM: Glycine max

<400> SEQUENCE: 29

Ala Ser Leu
1

<210> SEQ ID NO 30
<211> LENGTH: 3
<212> TYPE: PRT
<213> ORGANISM: Glycine max

<400> SEQUENCE: 30

Ala Thr Leu
1

<210> SEQ ID NO 31
<211> LENGTH: 3
<212> TYPE: PRT
<213> ORGANISM: Glycine max

<400> SEQUENCE: 31

Leu Gly Glu
1

<210> SEQ ID NO 32
<211> LENGTH: 2
<212> TYPE: PRT
<213> ORGANISM: Glycine max

<400> SEQUENCE: 32

Phe Tyr
```

```
<210> SEQ ID NO 33
<211> LENGTH: 2
<212> TYPE: PRT
<213> ORGANISM: Glycine max

<400> SEQUENCE: 33

Tyr Phe
1

<210> SEQ ID NO 34
<211> LENGTH: 3
<212> TYPE: PRT
<213> ORGANISM: Glycine max

<400> SEQUENCE: 34

Val Val Leu
1

<210> SEQ ID NO 35
<211> LENGTH: 3
<212> TYPE: PRT
<213> ORGANISM: Glycine max

<400> SEQUENCE: 35

Ser Ile Leu
1

<210> SEQ ID NO 36
<211> LENGTH: 3
<212> TYPE: PRT
<213> ORGANISM: Glycine max

<400> SEQUENCE: 36

Leu Ser Leu
1

<210> SEQ ID NO 37
<211> LENGTH: 4
<212> TYPE: PRT
<213> ORGANISM: Glycine max

<400> SEQUENCE: 37

Val Gly Gly Leu
1

<210> SEQ ID NO 38
<211> LENGTH: 3
<212> TYPE: PRT
<213> ORGANISM: Glycine max

<400> SEQUENCE: 38

Leu Ser Glu
1

<210> SEQ ID NO 39
<211> LENGTH: 3
<212> TYPE: PRT
<213> ORGANISM: Glycine max

<400> SEQUENCE: 39

Val Ala Tyr
1
```

```
<210> SEQ ID NO 40
<211> LENGTH: 3
<212> TYPE: PRT
<213> ORGANISM: Glycine max

<400> SEQUENCE: 40

Val Ser Phe
1

<210> SEQ ID NO 41
<211> LENGTH: 3
<212> TYPE: PRT
<213> ORGANISM: Glycine max

<400> SEQUENCE: 41

Tyr Ile Ala
1

<210> SEQ ID NO 42
<211> LENGTH: 3
<212> TYPE: PRT
<213> ORGANISM: Glycine max

<400> SEQUENCE: 42

Lys Val Gln
1

<210> SEQ ID NO 43
<211> LENGTH: 3
<212> TYPE: PRT
<213> ORGANISM: Glycine max

<400> SEQUENCE: 43

Phe Val Asp
1
```